US00RE46962E

(19) United States
(12) Reissued Patent
Townsend et al.

(10) Patent Number: US RE46,962 E
(45) Date of Reissued Patent: Jul. 24, 2018

(54) SURGICAL FORCEPS

(71) Applicant: Covidien LP, Mansfield, MA (US)

(72) Inventors: Jeffrey R. Townsend, Loveland, CO (US); Grant T. Sims, Littleton, CO (US); Chase Collings, Hayden, ID (US)

(73) Assignee: Covidien LP, Mansfield, MA (US)

(21) Appl. No.: 15/693,698

(22) Filed: Sep. 1, 2017

Related U.S. Patent Documents

Reissue of:
(64) Patent No.: 9,119,630
Issued: Sep. 1, 2015
Appl. No.: 14/064,702
Filed: Oct. 28, 2013

U.S. Applications:
(63) Continuation of application No. 13/091,331, filed on Apr. 21, 2011, now Pat. No. 8,568,408.

(51) Int. Cl.
*A61B 18/14* (2006.01)
*A61B 17/29* (2006.01)
*A61B 18/00* (2006.01)

(52) U.S. Cl.
CPC ..... *A61B 18/1445* (2013.01); *A61B 18/00* (2013.01); *A61B 18/1442* (2013.01); *A61B 17/29* (2013.01); *A61B 2017/2926* (2013.01)

(58) Field of Classification Search
None
See application file for complete search history.

(56) References Cited

U.S. PATENT DOCUMENTS 2,723,666 A * 11/1955 Greenberg ..... A61B 17/44 606/1
3,503,396 A * 3/1970 Pierie ..... A61B 17/282 24/517
3,503,398 A * 3/1970 Raible ..... A61B 17/282 606/207

(Continued)

FOREIGN PATENT DOCUMENTS

CN 201299462 9/2009
CN 201299462 Y 9/2009

(Continued)

OTHER PUBLICATIONS

U.S. Appl. No. 09/387,883, filed Sep. 1, 1999, Dale F. Schmaltz, abandoned.

(Continued)

*Primary Examiner* — Glenn K Dawson

(57) ABSTRACT

A forceps includes an end effector assembly having first and second jaw members. One (or both) of the first and second jaw members is moveable relative to the other between a spaced-apart position and an approximated position for grasping tissue therebetween. One (or both) of the jaw members includes a jaw frame a disposable jaw housing and an elastomeric ring member. The disposable jaw housing is releasably engageable with the jaw frame. The elastomeric ring member is removably positionable about a distal end of the jaw housing. The elastomeric ring member is configured to define a gap distance between the first and second jaw members upon movement of the first and second jaw members to the approximated position.

24 Claims, 7 Drawing Sheets

(56) References Cited

U.S. PATENT DOCUMENTS 3,653,389 A * 4/1972 Shannon ..... A61B 17/30 294/99.2
3,746,002 A * 7/1973 Haller ..... A61B 17/282 24/518
D249,549 S 9/1978 Pike
D263,020 S 2/1982 Rau, III
D295,893 S 5/1988 Sharkany et al.
D295,894 S 5/1988 Sharkany et al.
D298,353 S 11/1988 Manno
D299,413 S 1/1989 DeCarolis
4,821,719 A 4/1989 Fogarty ..... A61B 17/122 606/158
5,250,072 A * 10/1993 Jain ..... A61B 17/282 606/205
D343,453 S 1/1994 Noda
D348,930 S 7/1994 Olson
D349,341 S 8/1994 Lichtman et al.
D354,564 S 1/1995 Medema
D358,887 S 5/1995 Feinberg
5,551,622 A * 9/1996 Yoon ..... A61B 17/072 227/176.1
5,569,274 A 10/1996 Rapacki et al.
D384,413 S 9/1997 Zlock et al.
5,662,260 A * 9/1997 Yoon ..... A61B 17/072 227/176.1
H1745 H 8/1998 Paraschac
D402,028 S 12/1998 Grimm et al.
D408,018 S 4/1999 McNaughton
5,891,142 A * 4/1999 Eggers ..... A61B 18/1442 606/51
D416,089 S 11/1999 Barton et al.
6,007,552 A * 12/1999 Fogarty ..... A61B 17/02 606/157
D424,694 S 5/2000 Tetzlaff et al.
D425,201 S 5/2000 Tetzlaff et al.
6,099,539 A * 8/2000 Howell ..... A61B 17/122 606/151
H1904 H 10/2000 Yates et al.
6,193,732 B1 * 2/2001 Frantzen et al. ... A61B 17/1227 606/151
6,206,896 B1 * 3/2001 Howell ..... A61B 17/122 606/151
D449,886 S 10/2001 Tetzlaff et al.
6,312,445 B1 * 11/2001 Fogarty ..... A61B 17/02 606/157
D453,923 S 2/2002 Olson
D454,951 S 3/2002 Bon
6,368,340 B2 * 4/2002 Malecki ..... A61B 17/00234 606/204
D457,958 S 5/2002 Dycus et al.
D457,959 S 5/2002 Tetzlaff et al.
6,387,106 B1 * 5/2002 Howell ..... A61B 17/122 606/151
6,387,112 B1 * 5/2002 Fogarty ..... A61B 17/282 606/207
H2037 H 7/2002 Yates et al.
D465,281 S 11/2002 Lang
D466,209 S 11/2002 Bon
6,500,176 B1 * 12/2002 Truckai ..... A61B 18/1445 606/205
6,579,304 B1 * 6/2003 Hart ..... A61B 17/02 606/157
D493,888 S 8/2004 Reschke
D496,997 S 10/2004 Dycus et al.
D499,181 S 11/2004 Dycus et al.
D502,994 S 3/2005 Blake, III
D509,297 S 9/2005 Wells
6,989,017 B2 * 1/2006 Howell ..... A61B 17/122 606/151
D525,361 S 7/2006 Hushka
D531,311 S 10/2006 Guerra et al.
D533,274 S 12/2006 Visconti et al.
D533,942 S 12/2006 Kerr et al.
D535,027 S 1/2007 James et al.
D538,932 S 3/2007 Malik
D541,418 S 4/2007 Schechter et al.
D541,611 S 5/2007 Aglassinge
D541,938 S 5/2007 Kerr et al.
D545,432 S 6/2007 Watanabe
D547,154 S 7/2007 Lee
D564,662 S 3/2008 Moses et al.
D567,943 S 4/2008 Moses et al.
D575,395 S 8/2008 Hushka
D575,401 S 8/2008 Hixson et al.
D582,038 S 12/2008 Swoyer et al.
D617,900 S 6/2010 Kingsley et al.
D617,901 S 6/2010 Unger et al.
D617,902 S 6/2010 Twomey et al.
D617,903 S 6/2010 Unger et al.
D618,798 S 6/2010 Olson et al.
D621,503 S 8/2010 Otten et al.
776,910 A1 8/2010 Hixson et al.
7,766,910 B2 8/2010 Hixson et al.
D627,462 S 11/2010 Kingsley
D628,289 S 11/2010 Romero
D628,290 S 11/2010 Romero
D630,324 S 1/2011 Reschke
8,092,473 B2 * 1/2012 Hart ..... A61B 17/122 606/157
8,568,408 B2 * 10/2013 Townsend et al. ..... 606/48
9,636,169 B2 * 5/2017 Allen, IV ..... A61B 18/1447
2001/0016750 A1 * 8/2001 Malecki ..... A61B 17/00234 606/158
2002/0045909 A1 * 4/2002 Kimura et al. ..... 606/151
2002/0173805 A1 * 11/2002 Matsuno et al. ..... 606/151
2002/0177861 A1 * 11/2002 Sugiyama et al. ..... 606/151
2003/0073987 A1 * 4/2003 Sakurai ..... A61B 17/320068 606/28
2005/0113826 A1 5/2005 Johnson et al.
2005/0113828 A1 * 5/2005 Shields ..... A61B 18/1442 606/51
2006/0155274 A1 * 7/2006 Swanson ..... A61B 18/1442 606/51
2006/0217709 A1 9/2006 Couture et al.
2007/0173814 A1 7/2007 Hixson et al.
2009/0125026 A1 * 5/2009 Rioux ..... A61B 18/1442 606/45
2009/0275958 A1 * 11/2009 Harada et al. ..... 606/142
2010/0100122 A1 4/2010 Hinton
2014/0128867 A1 * 5/2014 Collings ..... A61B 17/285 606/52
2015/0250527 A1 * 9/2015 Sims ..... A61B 17/285 606/51

FOREIGN PATENT DOCUMENTS

DE 2415263 A1 10/1975
DE 02514501 A1 10/1976
DE 2627679 A1 1/1977
DE 03423356 C2 6/1986
DE 03612646 A1 4/1987
DE 8712328 U1 2/1988
DE 04303882 C2 2/1995
DE 04403252 A1 8/1995
DE 19515914 C1 7/1996
DE 19506363 A1 8/1996
DE 29616210 U1 11/1996
DE 19608716 C1 4/1997
DE 19751106 A1 5/1998
DE 19751108 A1 5/1999
DE 10045375 C2 10/2002
DE 202007009165 U1 8/2007
DE 202007009317 U1 8/2007
DE 202007016233 U1 1/2008
DE 19738457 B4 1/2009
DE 102004026179 B4 1/2009
DE 102008018406 B3 7/2009
EP 1 159 926 A2 12/2001
EP 1159926 A3 3/2003
EP 1532933 A1 5/2005
JP 61-501068 9/1984

(56) References Cited

FOREIGN PATENT DOCUMENTS

| | | | |
|---|---|---|---|
| JP | 10-24051 | A | 1/1989 |
| JP | 11-47150 | A | 6/1989 |
| JP | 6-502328 | | 3/1992 |
| JP | 5-5106 | | 1/1993 |
| JP | 05-40112 | | 2/1993 |
| JP | 6-121797 | A | 5/1994 |
| JP | 6-285078 | A | 10/1994 |
| JP | 6-511401 | | 12/1994 |
| JP | 06343644 | A | 12/1994 |
| JP | 07265328 | A | 10/1995 |
| JP | 8-56955 | | 5/1996 |
| JP | H08-56955 | | 5/1996 |
| JP | 08252263 | A | 10/1996 |
| JP | 8-317934 | A | 12/1996 |
| JP | 9-10223 | C | 1/1997 |
| JP | 910223 | | 1/1997 |
| JP | 9-122138 | A | 5/1997 |
| JP | H10-24051 | A | 1/1998 |
| JP | 10-155798 | A | 6/1998 |
| JP | 11-070124 | A | 3/1999 |
| JP | 11-169381 | A | 6/1999 |
| JP | 11-192238 | A | 7/1999 |
| JP | 11244298 | A | 9/1999 |
| JP | 2000-102545 | A | 4/2000 |
| JP | 2000342599 | A | 12/2000 |
| JP | 2000350732 | A | 12/2000 |
| JP | 2001128990 | A | 5/2001 |
| JP | 2001-190564 | A | 7/2001 |
| JP | 2004-517668 | A | 6/2004 |
| JP | 2004-528869 | A | 9/2004 |
| SU | 401367 | A1 | 10/1973 |
| WO | 0036986 | A1 | 6/2000 |
| WO | 0115614 | A1 | 3/2001 |
| WO | 0154604 | A1 | 8/2001 |
| WO | 2005/110264 | A2 | 11/2005 |
| WO | 05110264 | A3 | 4/2006 |

OTHER PUBLICATIONS

U.S. Appl. No. 12/336,970, filed Dec. 17, 2008, Paul R. Sremeich, abandoned.
U.S. Appl. No. 12/770,380, filed Apr. 29, 2010, Glenn A. Homer, abandoned.
Int'l Search Report EP 10 160870.1 dated Aug. 9, 2010.
U.S. Appl. No. 12/877,199, filed Sep. 8, 2010, Arlen J. Reschke, abandoned.
U.S. Appl. No. 12/947,352, filed Nov. 16, 2010, Jason L. Craig, abandoned.
U.S. Appl. No. 12/981,787, filed Dec. 30, 2010, John R. Twomey, abandoned.
U.S. Appl. No. 13/029,390, filed Feb. 17, 2011, Michael C. Moses.
European Search Report from corresponding Application EP 12 16 4917 dated Jan. 25, 2013.
"Electrosurgery: A Historical Overview" Innovations in Electrosurgery; Sales/Product Literature; Dec. 31, 2000. (6 pages).
Heniford et al. "Initial Results with an Electrothermal Bipolar Vessel Sealer" Surgical Endoscopy (2000) 15:799-801. (4 pages).
"Reducing Needlestick Injuries in the Operating Room" Sales/Product Literature 2001. (1 page).
Barbara Levy, "Use of a New Vessel Ligation Device During Vaginal Hysterectomy" FIGO 2000, Washington, D.C.. (1 page).
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report from corresponding Application EP 12 16 4917 mailed Jan. 25, 2013.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.

(56) References Cited

OTHER PUBLICATIONS

Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrochemical Bipolar Vessel Sealer" Oct. 1999.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 13/006,538, filed Jan. 14, 2011, John W. Twomey.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.

(56) References Cited

OTHER PUBLICATIONS

U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Peterson et al. "Comparison of Healing Process Following Ligation with Sutures and Bipolar Vessel Sealing" Surgical Technology International (2001).
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Homer.
U.S. Appl. No. 12/769,444, filed Apr. 28, 2010, Glenn A. Norner.
U.S. Appl. No. 12/770,369, filed Apr. 29, 2010, Glenn A. Homer.
U.S. Appl. No. 12/770,387, filed Apr. 29, 2010, Glenn A. Homer.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Homer.
U.S. Appl. No. 12/792,051, filed Jun. 2, 2010, David M. Garrison.
U.S. Appl. No. 12/792,068, filed Jun. 2, 2010, Glenn A. Homer.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.

* cited by examiner

SURGICAL FORCEPS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a continuation application of U.S. patent application Ser. No. 13/091,331, filed on Apr. 21, 2011, the entire contents of which are hereby incorporated by reference herein.

BACKGROUND

The present disclosure relates to a surgical forceps and, more particularly, to a surgical forceps including replaceable jaw members.

TECHNICAL FIELD

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

Generally, surgical instruments, including forceps, can be classified as single-use instruments, e.g., instruments that are discarded after a single use, partially-reusable instruments, e.g., instruments including both disposable portions and portions that are sterilizable for reuse, and completely reusable instruments, e.g., instruments that are completely sterilizable for repeated use. As can be appreciated, those instruments (or components of instruments) that can be sterilized and reused help reduce the costs associated with the particular surgical procedure for which they are used. However, although reusable surgical instruments are cost-effective, it is important that these instruments be capable of performing the same functions as their disposable counterparts and that any disposable components of these instruments be removable and replaceable with new components efficiently and easily.

SUMMARY

In accordance with one embodiment of the present disclosure, a forceps is provided. The forceps includes an end effector assembly having first and second jaw members. One (or both) of the jaw members is moveable relative to the other between a spaced-apart position and an approximated position for grasping tissue therebetween. One (or both) of the jaw members includes a jaw frame, a jaw housing, and an elastomeric ring member. The jaw housing is releasably engageable with the jaw frame. The elastomeric ring member is removably positionable about a distal end of the jaw housing. The elastomeric ring member is configured to define a gap distance between the first and second jaw members upon movement of the first and second jaw members to the approximated position.

In one embodiment, the gap distance is in the range of about 0.001 inches to about 0.006 inches.

In another embodiment, the jaw housing includes an electrically-conductive seal plate releasably engageable therewith. The seal plate may be adapted to connect to a source of electrosurgical energy for sealing tissue.

The jaw housing may further include an insulating member releasably engageable therewith. The insulating member is configured to releasably retain the seal plate thereon.

In another embodiment, the jaw housing is slidably positionable about the seal plate, the insulating member, and the jaw frame to releasably secure the seal plate, the insulating member, and the jaw frame to one another.

In yet another embodiment, the insulating member is formed at least partially from a resiliently compressible material configured to be compressed upon slidable positioning of the jaw housing about the seal plate, the insulating member and the jaw frame to releasably secure the seal plate, the insulating member and the jaw frame to one another in a friction-fit engagement.

In still another embodiment, the insulating member is configured to snap-fittingly engage the jaw housing upon slidable positioning of the jaw housing about the seal plate, the insulating member and the jaw frame to releasably secure the seal plate, the insulating member and the jaw frame to one another.

In still yet another embodiment, the insulator includes a proximal stop feature configured to define a proximal gap distance between the first and second jaw members upon movement of the first and second jaw members to the approximated position. In such an embodiment, the elastomeric ring member defines a distal gap distance between the first and second jaw members upon movement of the first and second jaw members to the approximated position.

In another embodiment, the seal plate and the insulating member include longitudinally-extending channels defined therethrough. The longitudinally-extending channels defined within the seal plate and the insulating member are configured to permit reciprocation of a knife therethrough.

A method of assembling a jaw member of a forceps is also provided in accordance with the present disclosure. The method includes releasably engaging a jaw housing to a jaw frame. The method further includes positioning an elastomeric ring member about the jaw housing toward a distal end thereof. The elastomeric ring member is configured to define a gap distance between the jaw member and an opposed jaw member of the forceps when the jaw members are moved to an approximated position.

In one embodiment, the gap distance is in the range of about 0.001 inches to about 0.006 inches.

In another embodiment, the jaw housing includes an electrically-conductive seal plate releasably engageable therewith. The seal plate may be adapted to connect to a source of electrosurgical energy for sealing tissue. The jaw housing may further include an insulating member releasably engageable therewith. The insulating member is configured to retain the seal plate thereon.

In another embodiment, releasably engaging the jaw housing to the jaw frame further includes positioning the insulating member about the jaw frame, positioning the seal plate about the insulating member, and slidably positioning the jaw housing about the seal plate, the insulating member, and the jaw frame to releasably secure the seal plate, the insulating member, and the jaw frame to one another.

In still another embodiment, the insulating member is formed partially (or entirely) from a resiliently compressible material. In such an embodiment, the insulating member is configured to be compressed upon slidable positioning of the jaw housing about the seal plate, the insulating member and the jaw frame to thereby releasably secure the seal plate, the insulating member and the jaw frame to one another in a friction-fit engagement.

In still yet another embodiment, the insulating member is configured to snap-fittingly engage the jaw housing upon slidable positioning of the jaw housing about the seal plate, the insulating member and the jaw frame to secure the seal plate, the insulating member and the jaw frame to one another.

In yet another embodiment, the method further includes disengaging the jaw housing from the jaw frame, releasably engaging a second jaw housing to the jaw frame, and positioning a second elastomeric ring member about the second jaw housing toward a distal end thereof. The second elastomeric ring member, similar to the first elastomeric ring member, is configured to define a gap distance between the jaw member and the opposed jaw member of the forceps when the jaw members are moved to the approximated position.

In another embodiment of a forceps provided in accordance with the present disclosure, an end effector assembly includes first and second jaw members. One (or both) of the jaw members is moveable relative to the other between a spaced-apart position and an approximated position for grasping tissue therebetween. One (or both) of the jaw members includes a jaw frame, a jaw housing and an elastomeric ring member. The ring member is removably positionable about a distal end of the jaw housing to releasably secure the jaw housing to the jaw frame. The elastomeric ring member is also configured to define a gap distance between the first and second jaw members upon movement of the first and second jaw members to the approximated position.

Similar to the previous embodiments, the forceps may also include an insulating member and a seal plate. In such embodiments, the insulating member, the jaw housing and/or the jaw frame may include a ring receiving feature defined therein and configured to retain the elastomeric ring member in position thereon. The forceps may otherwise be configured similarly to any of the other embodiments described above.

Another embodiment of a method of assembling a jaw member of a forceps is provided in accordance with the present disclosure. The method includes positioning a jaw housing about a jaw frame and positioning an elastomeric ring member about the jaw housing to releasably secure the jaw housing to the jaw frame. The elastomeric ring member is also configured to define a gap distance between the jaw member and an opposed jaw member of the forceps when the jaw members are moved to an approximated position. The method may further include any of the features of any of the other embodiments discussed above.

BRIEF DESCRIPTION OF THE DRAWINGS

Various embodiments of the present disclosure are described herein with reference to the drawings wherein.

DETAILED DESCRIPTION

Figure 1:
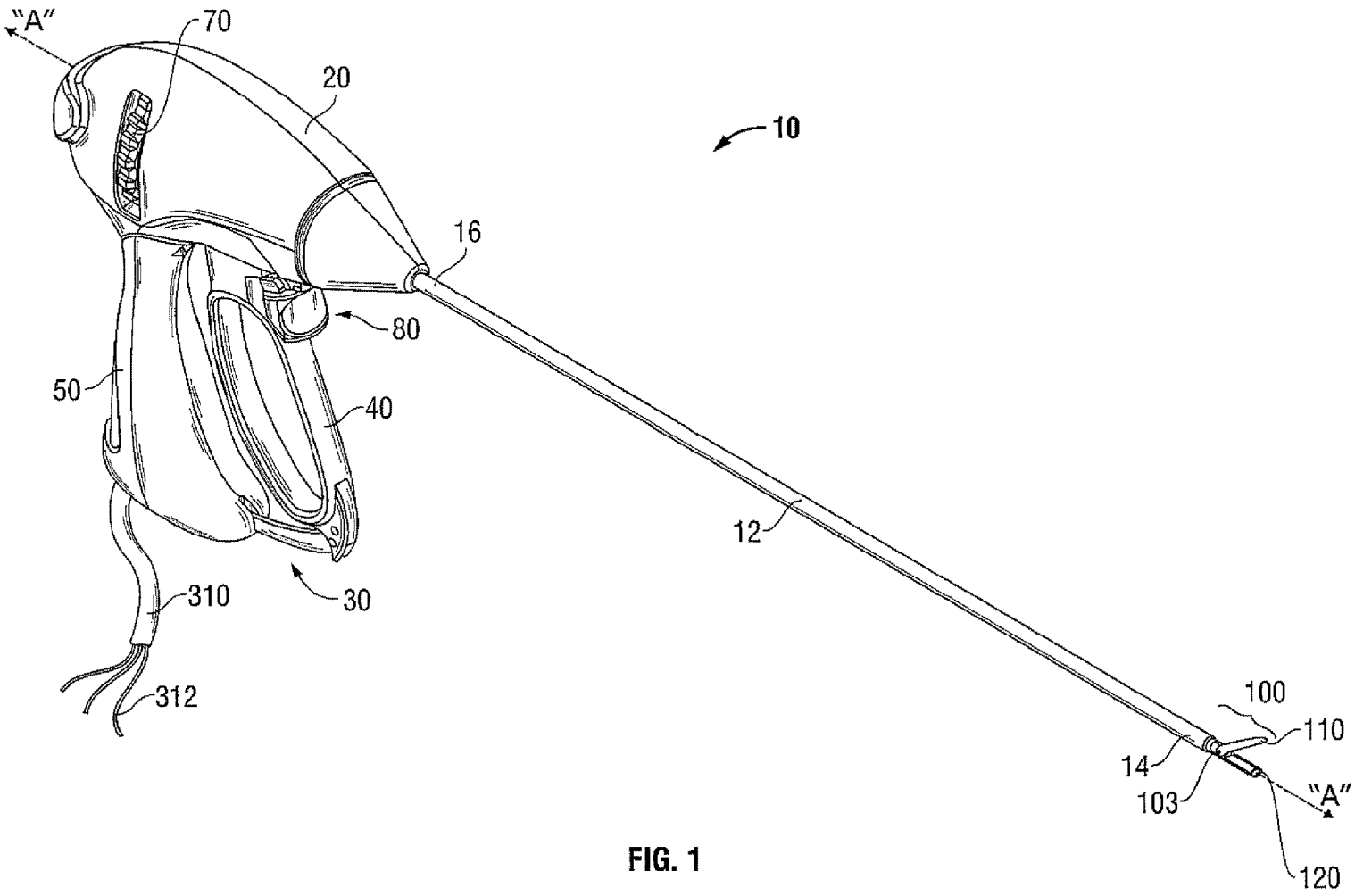
FIG. 1 is a front, perspective view of an endoscopic surgical forceps configured for use in accordance with the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
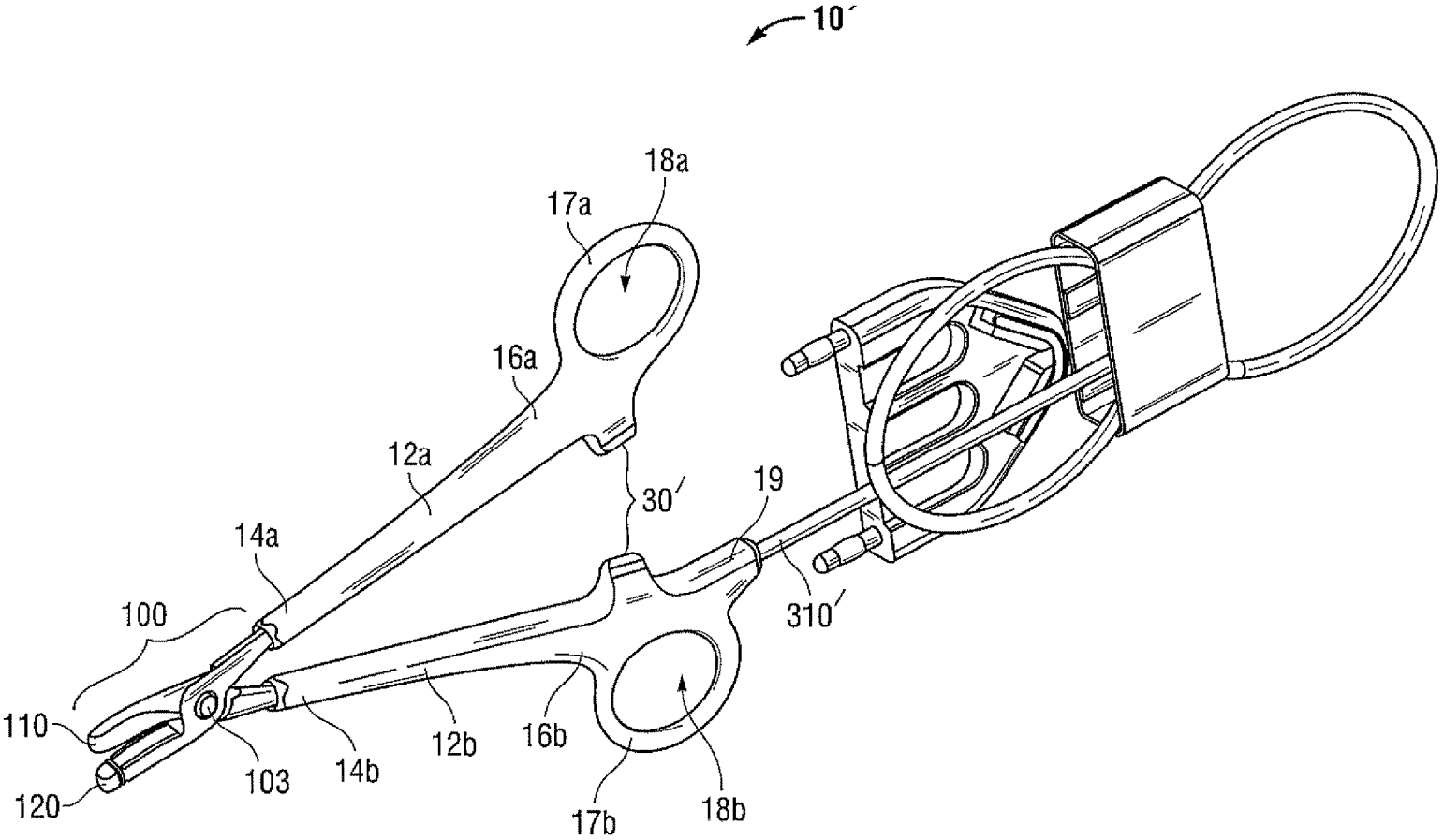
FIG. 2 is a front, perspective view of an open surgical forceps configured for use in accordance with the present disclosure.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic instrument, e.g., forceps 10, or an open instrument, e.g., forceps 10', may be utilized in accordance with the present disclosure. Obviously, different electrical and mechanical connections and considerations apply to each particular type of instrument, however, the novel aspects with respect to the end effector assembly and its operating characteristics remain generally consistent with respect to both the open and endoscopic configurations.

Turning now to FIG. 1, an endoscopic forceps 10 is provided defining a longitudinal axis "A-A" and including a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 310 that connects forceps 10 to a generator (not shown) or other suitable power source, although forceps 10 may alternatively be configured as a battery powered instrument. Cable 310 includes a wire (or wires) 312 extending therethrough that has sufficient length to extend through shaft 12 in order to provide electrical energy to at least one of the jaw members 110 and 120 of end effector assembly 100.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about a longitudinal axis "A-A" to rotate end effector 100 about longitudinal axis "A-A." The housing 20 houses the internal working components of the forceps 10.

Figure 3A:
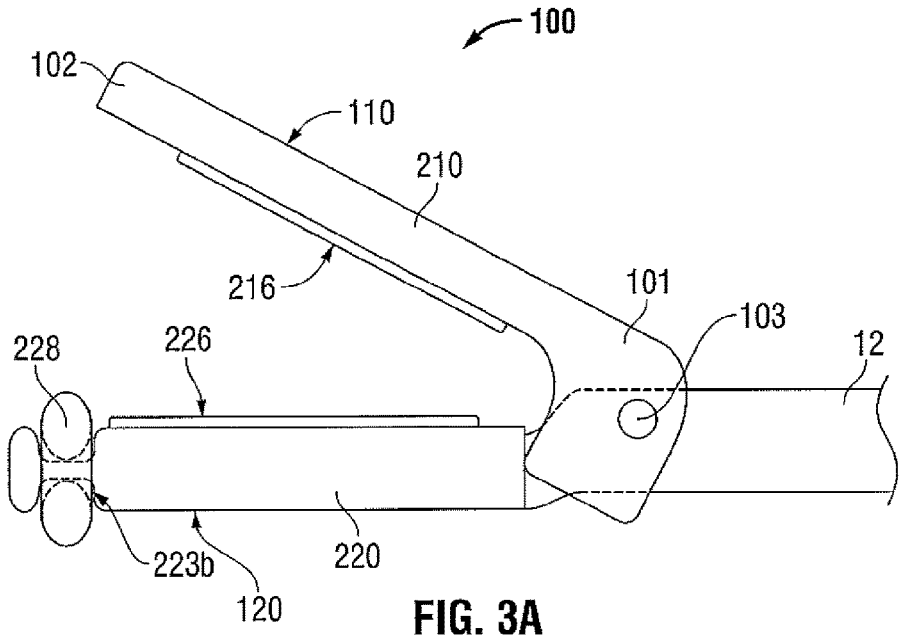
FIG. 3A is a side view of an end effector assembly configured for use with either of the forceps of FIGS. 1 and 2 wherein jaw members of the end effector assembly are shown in a spaced-apart position.
Figure 3B:
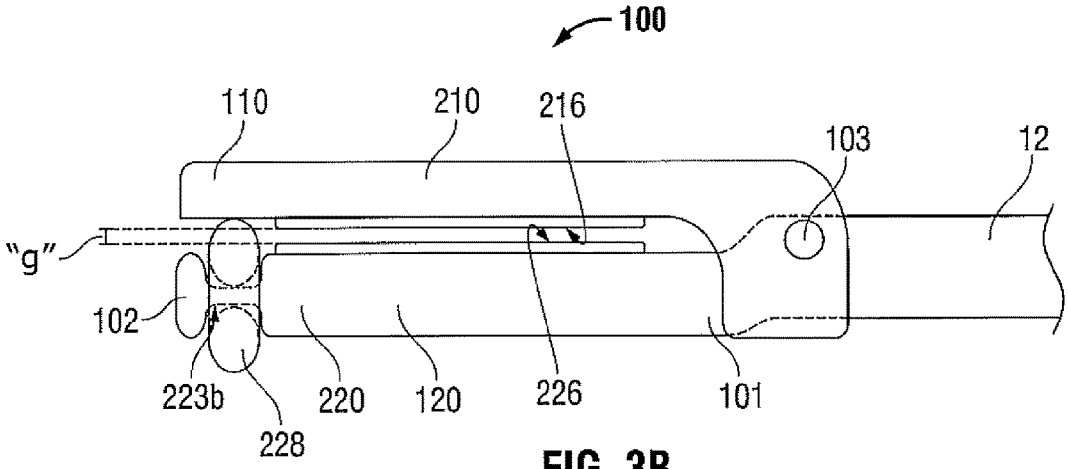
FIG. 3B is a side view of the end effector assembly of FIG. 3A wherein the jaw members are shown in an approximated position.
Figure 5:
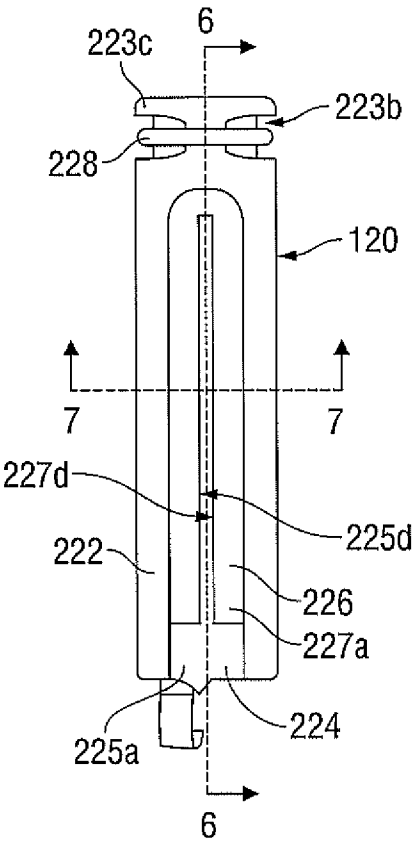
FIG. 5 is a top view of the jaw member of FIG. 4.
Figure 4:
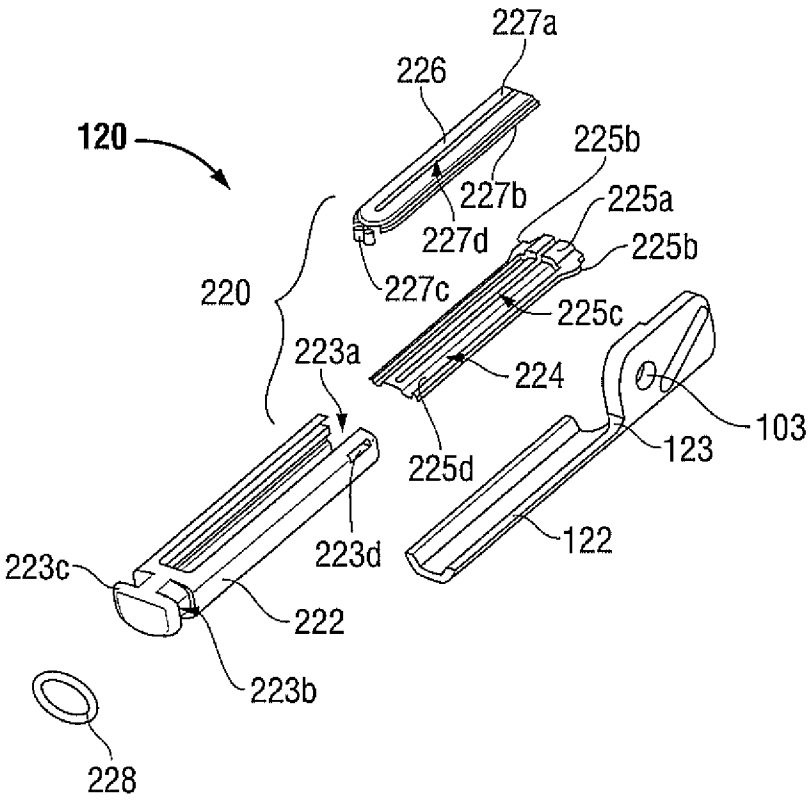
FIG. 4 is an exploded view of one of the jaw members of the end effector assembly of FIG. 3A.

Referring momentarily to FIGS. 3-4, end effector assembly 100 is shown attached at a distal end 14 of shaft 12 and includes a pair of opposing jaw members 110 and 120. Each of jaw members 110 and 120 includes an opposed electrically conductive tissue sealing surface 216, 226, respectively. End effector assembly 100 is designed as a unilateral assembly, i.e., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, i.e., where both jaw member 110 and j aw member 120 are moveable about a pivot 103 relative to one another and to shaft 12. In some embodiments, a knife assembly (not shown) is disposed within shaft 12 and a knife channel (FIG. 7) is defined within one or both jaw members 110, 120 to permit reciprocation of a knife blade (not shown) therethrough. End effector assembly 100 will be described in greater detail hereinbelow.

Referring again to FIG. 1, moveable handle 40 of handle assembly 30 is ultimately connected to a drive assembly (not shown) that, together, mechanically cooperate to impart movement of jaw members 110 and 120 between a spaced-apart position (FIG. 3A) and an approximated position (FIG. 3B) to grasp tissue disposed between sealing surfaces 216 and 226 (FIGS. 3A-3B) of jaw members 110, 120, respectively. As shown in FIG. 1, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position (FIG. 3B) of jaw members 110, 120.

Referring now to FIG. 2, an open forceps 10' is shown including two elongated shafts 12a and 12b, each having a proximal end 16a and 16b, and a distal end 14a and 14b, respectively. Similar to forceps 10 (FIG. 1), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably connected about a pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another that, in turn, pivots jaw members 110 and 120 from an open position (FIG. 3A), wherein the jaw members 110 and 120 are disposed in spaced-apart relation relative to one another, to a closed position (FIG. 3B), wherein the jaw members 110 and 120 cooperate to grasp tissue therebetween.

A ratchet 30' may be included for selectively locking the jaw members 110 and 120 relative to one another at various positions during pivoting. It is envisioned that the ratchet 30' may include graduations or other visual markings that enable the user to easily and quickly ascertain and control the amount of closure force desired between the jaw members 110 and 120.

With continued reference to FIG. 2, one of the shafts, e.g., shaft 12b, includes a proximal shaft connector 19 which is designed to connect the forceps 10' to a source of electrosurgical energy such as an electrosurgical generator (not shown). Proximal shaft connector 19 secures an electrosurgical cable 310' to forceps 10' such that the user may selectively apply electrosurgical energy to the electrically conductive sealing surfaces 216 and 226 of jaw members 110 and 120, respectively, as needed.

Forceps 10' may further include a knife assembly (not shown) disposed within either of shafts 12a, 12b and a knife channel (FIG. 7) defined within one or both jaw members 110, 120 to permit reciprocation of a knife blade (not shown) therethrough.

Turning now to FIGS. 3A-7, as mentioned above, end effector assembly 100 including jaw members 110, 120 is configured for use with either forceps 10 or forceps 10', discussed above, or any other suitable surgical instrument capable of pivoting jaw members 110, 120 relative to one another between a spaced-apart position and an approximated position for grasping tissue therebetween. However, for purposes of simplicity and consistency, end effector assembly 100 will be described hereinbelow with reference to forceps 10 only.

Jaw members 110, 120 of end effector assembly 100 each include a disposable component 210, 220 that is releasably engageable with a jaw frame 112, 122, respectively. Jaw frames 112, 122, in turn, are pivotably coupled to one another about pivot 103. Disposable components 210, 220 are removable from jaw frames 112, 122, respectively, and are replaceable with new disposable components 210, 220, e.g., disposable components 210, 220 may be configured to be discarded and replaced after a single use (or a single procedure), while the remaining components of forceps 10 may be formed from a sterilizable material such that they may be sterilized, e.g., placed in an autoclave (not shown), after each procedure for repeat use in conjunction with subsequent sets of disposable components 210, 220, e.g., a second set of disposable components 210, 220. Alternatively, the remaining components of forceps 10 may likewise be disposable. In either embodiment, disposable components 210, 220 are advantageous in that the surgeon may select the disposable components 210, 220 for use with forceps 10 that are best suited for the particular procedure to be performed, i.e., the surgeon may customize forceps 10 to the particular procedure to be performed by selecting a particular set of disposable components 210, 220, without requiring an entirely new surgical instrument. For example, the surgeon may select between a first set of disposable components 210, 220 configured for a first surgical purpose and a second set of disposable components 210, 220 configured for a second, different surgical purpose, depending on the surgical procedure to be performed. As can be appreciated, requiring only a new set, i.e., a second set, of disposable components 210, 220 for each use, rather than an entire new surgical instrument, helps reduce the equipment costs associated with performing a particular surgical procedure. Likewise, the ability to interchangeably use different disposable components 210, 220, e.g., first and second sets of disposable components 210, 220, allows a single instrument to be customizable for use in various different procedures, rather than requiring a different instrument for each different procedure.

With continued reference to FIGS. 3A-7, disposable component 220 of jaw member 120 is described. Disposable component 220 generally includes an outer jaw housing 222, an insulator 224, an electrically-conductive tissue sealing plate 226, and a resiliently flexible ring 228, e.g., an elastomeric O-ring 228. As best shown in FIG. 4, jaw housing 222 is configured to mechanically engage insulator 224, tissue sealing plate 226 and jaw frame 122 to one another, e.g., in slidable snap-fit engagement therewith, although other mechanisms (not shown) for releasably securing jaw housing 222 about insulator 224, tissue sealing plate 226 and jaw frame 122 are contemplated. More specifically, jaw housing 222 includes an elongated cavity 223a defined therein for slidably receiving tissue sealing plate 226, insulator 224, and jaw frame 122 therethrough. Jaw housing 222 further includes an annular groove 223b defined therein toward a distal end 223c thereof for positioning of O-ring 228 thereon. The assembly of jaw member 120 will be described in greater detail below.

As best shown in FIG. 4, insulator 224 is configured to electrically isolate tissue sealing plate 226 from the remaining components of jaw member 120. Accordingly, insulator 224 is formed at least partially from an electrically-insulative material, e.g., silicon. Insulator 224 includes a base 225a disposed at a proximal end thereof. Base 225a includes a pair of laterally-extending, dovetail-shaped flanges 225b configured to snap-fittingly engage elongated slots 223d defined within jaw housing 222 to secure jaw housing 222 about insulator 224, tissue sealing plate 226 and jaw frame 122. Further, as will be described below, base 225a is configured to abut a proximal end 227a of tissue sealing plate 226 on an upper side thereof and to abut proximal end 123 of jaw frame 122 on the lower side thereof such that, when jaw housing 222 is slid over and snap-fittingly engaged with insulator 224, the components of jaw member 120, e.g., jaw frame 122, jaw housing 222, insulator 224 and tissue sealing plate 226, are maintained in substantially fixed relation relative to one another. Base 225a may also be configured to set a gap distance "g" (FIG. 3B) between jaw members 110, 120 at a proximal end 101 of end effector assembly 100 when jaw members 110, 120 are moved to the approximated position, as will be described in greater detail below.

Insulator 224 may alternatively, or additionally, be formed from a resiliently compressible material, e.g., silicon, that is compressed, e.g., from an initial state to a compressed state, upon insertion of insulator 224 into jaw housing 222 such that insulator 224, tissue sealing plate 226 and jaw frame 122 are frictionally retained within jaw housing 222, e.g., under the biasing force urging insulator 224 back toward the initial state. Further, insulator 224 may include a blade slot 225c defined therein for reciprocation of a knife blade (not shown) therethrough.

With continued reference to FIG. 4, tissue sealing plate 226 of disposable component 220 of jaw member 120 is configured for positioning about insulator 224 and for slidable insertion into jaw housing 222. More specifically, tissue sealing plate 226 includes a lip 227b extending from an outer periphery thereof that is configured to engage a track 225d defined within insulator 224 to retain tissue sealing plate 226 and insulator 224 in substantially fixed relation relative to one another. Tissue sealing plate 226 further includes a post 227c extending therefrom that is configured to electrically connect tissue sealing plate 226 to a source of electrosurgical energy (not shown), e.g., via wires 312 (FIG. 1) disposed within electrosurgical cable 310 (FIG. 1). A longitudinally-extending blade slot 227d configured for alignment with blade slot 225c defined within insulator 224 may also be provided to permit reciprocation of a knife blade (not shown) therethrough.

Referring again to FIGS. 3A and 3B, in conjunction with FIG. 4, O-ring 228, as mentioned above, is configured for positioning about jaw housing 222. More specifically, O-ring 228 is configured for positioning within annular groove 223b formed within jaw housing 222 toward distal end 223c thereof. O-ring 228 may be formed from any bio-compatible, resiliently flexible material, e.g., an elastomer. Further, although shown in the drawings as having an oval-shaped cross-sectional configuration, O-ring 228 may alternatively define a circular cross-sectional configuration, a polygonal cross-sectional configuration, or any other suitable cross-sectional configuration. Annular groove 223b may define a complementary configuration relative to O-ring 228, e.g., a semi-oval cross-sectional configuration, to facilitate positioning and retention of O-ring 228 within annular groove 223b.

As will be described in greater detail below, O-ring 228 may also be configured to provide a gap distance "g" between jaw members 110, 120 at a distal end 102 of end effector assembly 100, in conjunction with, or in place of base 225a of insulator 224 (FIG. 4). Accordingly, the compressibility of O-ring 228, in response to the closure force imparted thereto by jaw members 110, 120, determines, in part, the gap distance "g" between tissue sealing plates 216, 226 of members 110, 120, respectively. For example, the more compressible the O-ring 228, the smaller the gap distance "g" between sealing plates 216, 226 of jaw members 110, 120, respectively. The compressibility of the O-ring 228 may depend on various factors including the thickness, or diameter of the O-ring 228, the cross-sectional configuration of the O-ring, and/or the material(s) used to form the O-ring 228. Thus, the user may select an O-ring 228 configured to set a specific gap distance "g," or range of gap distances "g," suitable for the particular procedure to be performed. Various different O-rings 228, e.g., a first O-ring having a first configuration and a second O-ring having a second, different configuration, may be provided such that a single surgical instrument, e.g., forceps 10 (FIG. 1), may be customized for use, e.g., by selecting an appropriate O-ring, in a wide range of applications involving different tissue thicknesses, tissue compositions, and/or other anatomical considerations. Gap ranges are contemplated in the range of about 0.001 inches to about 0.006 inches.

Figure 7:
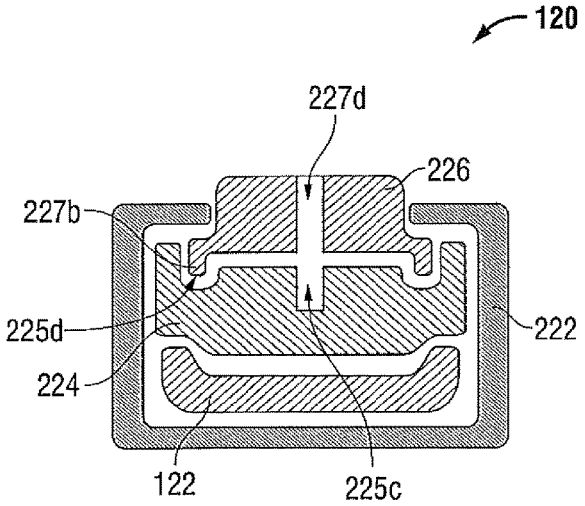
FIG. 7 is a transverse, cross-sectional view of the jaw member of FIG. 4.
Figure 9:
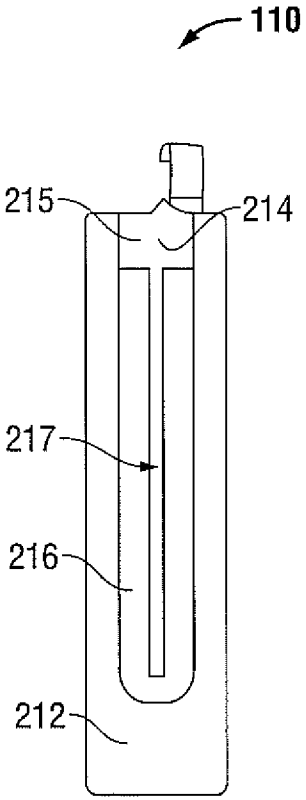
FIG. 9 is a top view of the jaw member of FIG. 8.
Figure 8:
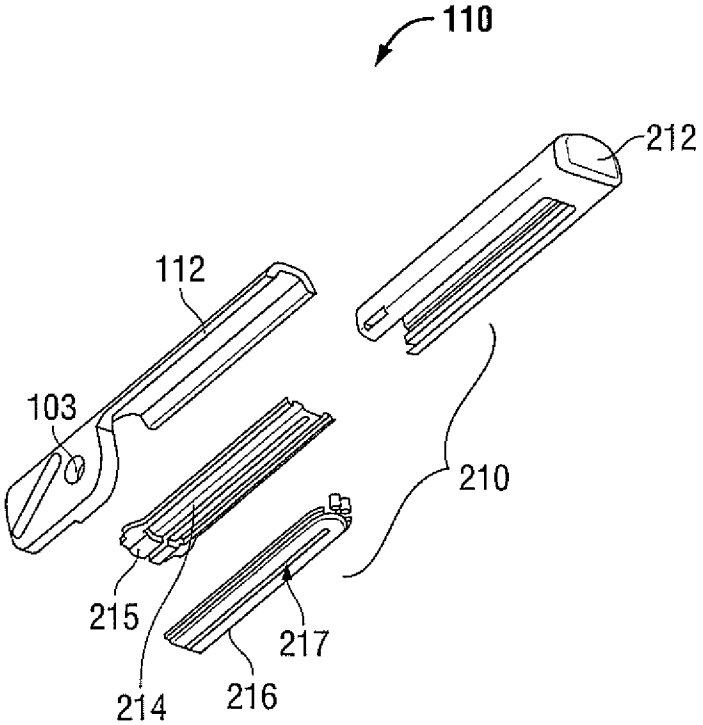
FIG. 8 is an exploded, perspective view of the other jaw member of the end effector assembly of FIG. 3A.

Turning now to FIGS. 8 and 9, jaw member 110 is shown. Jaw member 110 includes a jaw frame 112 and a disposable component 210 including an outer jaw housing 212, an insulator 214, and a tissue sealing plate 216. Jaw frame 112 is pivotably engageable with jaw frame 122 of jaw member 120 (FIGS. 4-7), about pivot 103 (FIGS. 3A-3B), to permit jaw members 110, 120 to move relative to one another between the spaced-apart position (FIG. 3A) and the approximated position (FIG. 3B). Insulator 214 is configured to retain tissue sealing plate 216 thereabout and includes a proximal base 215 for abutting tissue sealing plate 216 and jaw frame 112. Proximal base 215 may also be configured, in conjunction with proximal base 225a of insulator 224 of jaw member 120, to set the gap distance "g" between tissue sealing plates 216, 226 of jaw members 110, 120, respectively, at proximal end 101 of end effector assembly 100 (see FIG. 3B).

Jaw member 110 is configured similarly to jaw member 120 except that jaw member 110 does not include an O-ring disposed about jaw housing 212. However, jaw member 110 may alternatively be configured to include an O-ring in place of, or in addition to O-ring 228 of jaw member 120 (FIGS. 3A-3B). Further, tissue sealing plate 216 and insulator 214 of jaw member 110 may cooperate to define a blade channel 217 extending longitudinally therethrough such that, upon approximation of jaw members 110, 120, blade channel 217 and the blade channel of jaw member 120, e.g., the blade channel formed from blade slots 225c and 227d, cooperate with one another to permit reciprocation of a knife blade (not shown). Alternatively, the blade channel may be defined completely within one of jaw members 110, 120, e.g., such that the other jaw member defines a continuous configuration without a blade channel defined therein, or the blade channel may be left out entirely. Jaw member 110 may otherwise be configured similarly to jaw member 120 and, thus, the description of such will not be repeated herein for purposes of brevity.

Referring once again to FIGS. 4-7, the assembly of jaw member 120 is described. The assembly of jaw member 110 (FIGS. 8-9) is substantially similar to that of jaw member 120 and, thus, will not be repeated. Initially, tissue sealing plate 226 is positioned about insulator 224 such that lip 227b of tissue sealing plate 226 is disposed within track 225d of insulator 224 and such that proximal end 227a of tissue sealing plate 226 abuts base 225a of insulator 224. As can be appreciated, in this position, post 227c extends past insulator 224 on a distal end thereof, allowing post 227c to be coupled to a source of electrosurgical energy (not shown) for energizing tissue sealing plate 226.

Next, insulator 224 and tissue sealing plate 226 are positioned atop jaw frame 122 such that proximal end 123 of jaw frame 122 abuts base 225a of insulator 224. Accordingly, in this position, insulator 224 is inhibited from translating distally relative to jaw frame 122 and tissue sealing plate 226, due to the abutting relation of base 225a therewith.

With insulator 224 and tissue sealing plate 226 disposed about jaw frame 122, jaw housing 222 is slidably inserted over insulator 224, tissue sealing plate 226, and jaw frame 122. In other words, insulator 224, tissue sealing plate 226, and jaw frame 122 and slid into elongated cavity 223a defined within jaw housing 222. More specifically, insulator 224, tissue sealing plate 226, and jaw frame 122 are slid into elongated cavity 223a until lateral flanges 225b of insulator 224 snap into engagement with elongated slots 223d defined within jaw housing 222. An audible and/or tactile "snap," or other feedback signal, may be provided to alert the user that jaw housing 222 has been securely engaged about insulator 224, tissue sealing plate 226, and jaw frame 122. In this position, as best shown in FIG. 7, blade channels 225c, 227d of insulator 224 and tissue sealing plate 226, respectively, are aligned with one another to form a continuous blade channel for reciprocation of a knife blade (not shown) therethrough.

Once jaw housing 222 is secured about jaw frame 122, insulator 224 and tissue sealing plate 226, O-ring 228 may be slid over distal end 223c of member 120 and into position within annular groove 223b of jaw housing 222 to complete the assembly of jaw member 120. As mentioned above, the specific O-ring 228 chosen may depend on the desired gap distance "g" between tissue sealing plates 216, 226 of jaw members 110, 120, respectively, which, in turn, may depend on the size and/or composition of tissue to be sealed, the particular procedure to be performed, and/or other anatomical considerations.

Figure 6:
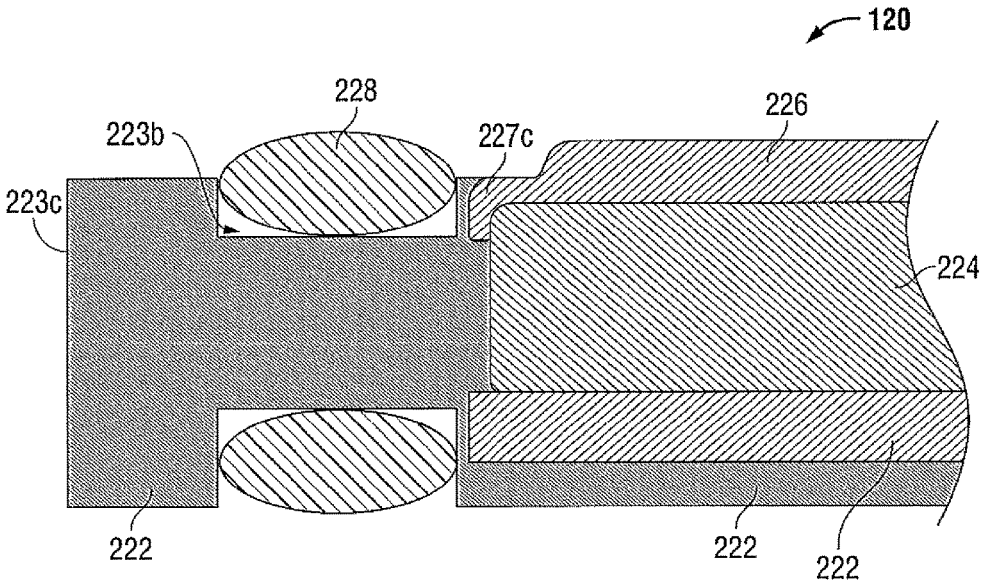
FIG. 6 is a longitudinal, cross-sectional view of the jaw member of FIG. 4.

As best shown in FIG. 7, with jaw member 120 in the fully assembled condition, jaw frame 122 and insulator 224 are disposed within jaw housing 222, while tissue sealing plate 226 extends therefrom toward jaw member 110 (FIGS. 3A-3B). O-ring 228, as best shown in FIGS. 3A-B and 6, likewise extends from jaw housing 222 toward jaw member 110 further than tissue sealing plate 226, e.g., O-ring 228 extends beyond tissue sealing plate 226. As can be appreciated, due to the various mechanical relationships between jaw frame 120, disposable component 220 and the subcomponents thereof, as discussed above, in the fully assembled condition, jaw frame 122, jaw housing 222, insulator 224, tissue sealing plate 226 and O-ring 228, are all retained in substantially fixed relation relative to one another.

Turning back to FIGS. 3A and 3B, the use and operation of end effector assembly 100 will be described. Initially, disposable components 210, 220 are assembled on jaw members 110, 120, respectively, as described above. Next, with jaw members 110, 120 in the spaced-apart position (FIG. 3A), end effector assembly 100 is positioned such that tissue to be grasped, sealed and/or divided is disposed between tissue sealing plates 216, 226 of jaw members 110, 120, respectively. Thereafter, jaw members 110, 120 are moved to the approximated position to grasp tissue between tissue sealing plates 216 and 226, e.g., via depressing moveable handle 40 of forceps 10 from the initial position to the depressed position relative to fixed handle 50 (see FIG. 1).

Upon moving jaw members 110, 120 to the approximated position, as shown in FIG. 3B, O-ring 228, which is disposed about jaw member 120, contacts jaw housing 212 of jaw member 110 towards distal end 102 of end effector assembly 100 to set the gap distance "g" between tissue sealing plates 216, 226 of jaw members 110, 120, respectively. Likewise, at the proximal end 101 of end effector assembly 100, proximal bases 215, 225a of respective insulators 214, 224 help maintain a uniform gap distance "g" between tissue sealing plates 216, 226 along the lengths of tissue sealing plates 216 and 226. However, only one of insulators 214, 224 of jaw members 110, 120, respectively, may include a proximal base that helps set gap distance "g," or neither of insulators 214, 224 may include a proximal base, e.g., only O-ring 228 may be used to set the gap distance "g."

With continued reference to FIG. 3B, and as mentioned above, upon approximation of jaw members 110, 120 to grasp tissue therebetween, O-ring 228 is compressed between jaw housings 212, 222, of jaw members 110, 120, respectively. As can be appreciated, the closure force imparted by jaw members 110, 120 and the specific configuration of O-ring 228 determines the amount of compression of O-ring 228 and, as a result, the gap distance "g" between tissue sealing plates 216, 226. Further, proximal bases 215, 225a, of insulators 214, 224 of jaw members 110, 120, respectively, may also be configured to compress in response to the closure force imparted thereon by jaw members 110, 120 to help define gap distance "g," or may simply be configured to define a minimum gap distance "g," thereby helping to ensure that tissue sealing plates 216, 226 of jaw members 110, 120, respectively, do not contact one another in the approximated position of jaw members 110, 120.

With tissue grasped between sealing plates 216, 226, of jaw members 110, 120, respectively, electrosurgical energy may be supplied to one (or both) of tissue sealing plates 216, 226 and through tissue to effect a tissue seal. As can be appreciated, controlling the gap distance "g" between sealing plates 216 and 226, e.g., via O-ring 228 and/or proximal bases 215, 225a, helps to ensure that an effective tissue seal is achieved. The gap distance "g" between opposing sealing plates 216 and 226 during sealing ranges from about 0.001 inches to about 0.006 inches.

In embodiments where a knife assembly (not shown) is provided, the knife blade (not shown) may then be advanced through the knife channels of jaw member 110 and/or jaw member 120 to cut tissue along the previously formed tissue seal. Thereafter, jaw members 110, 120 may be returned to the spaced-apart position to release the sealed and divided tissue and end effector assembly 100 may be removed from the surgical site. Finally, disposable components 210, 220 may be removed from the respective jaw frames 112, 122, e.g., with respect to disposable component 220, via disengaging lateral flanges 225b of insulator 224 from elongated slots 223d of jaw housing 222 and similarly with respect to disposable component 210, and discarded. After sterilization of forceps 10, a second set of disposable components 210, 220 (including a second O-ring 228) may be engaged thereon similarly as described above for performing subsequent procedures.

Figure 10:
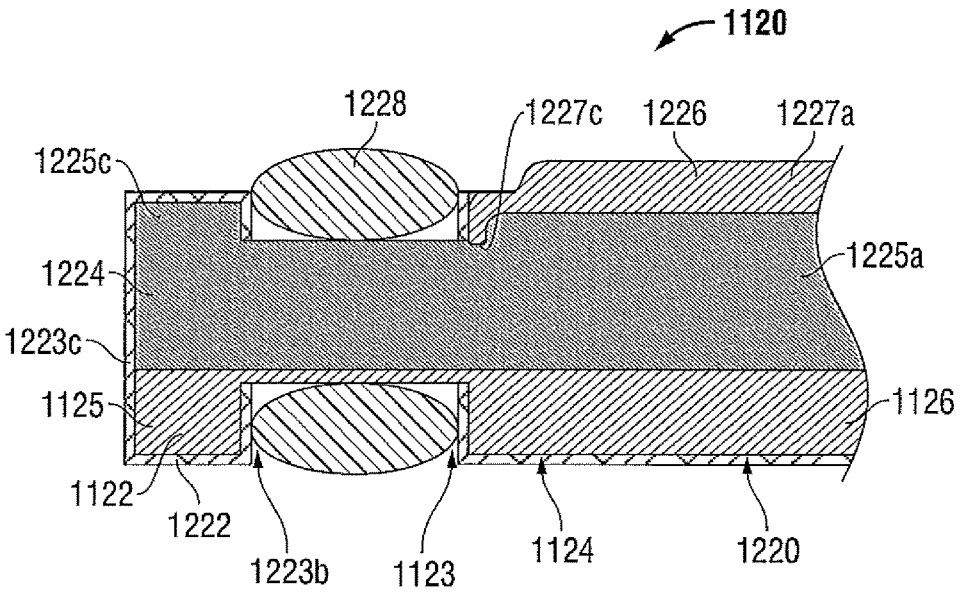
FIG. 10 is a longitudinal, cross-sectional view of another embodiment of a jaw member of an end effector assembly configured for use with either of the forceps of FIGS. 1 and 2.
Figure 11:
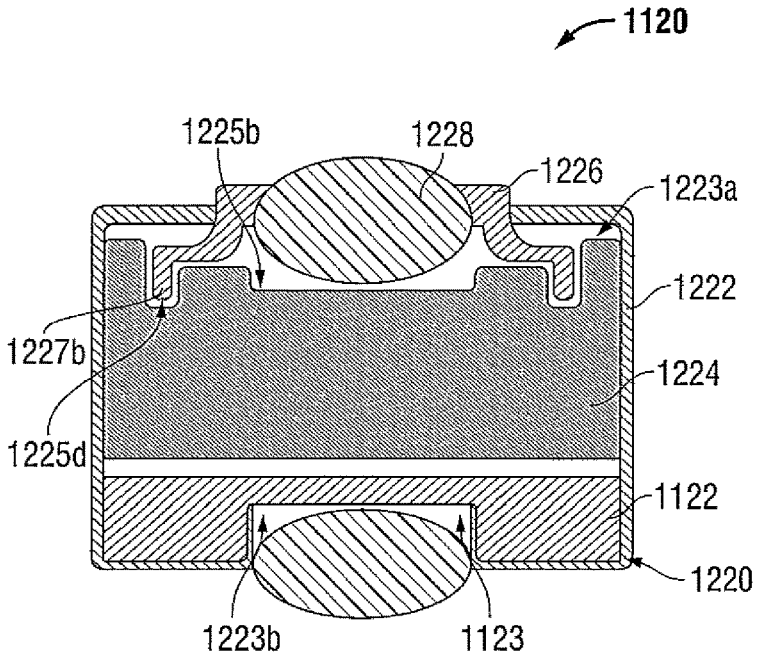
FIG. 11 is a transverse, cross-sectional view of the jaw member of FIG. 10.

Turning now to FIGS. 10 and 11, another embodiment of an end effector assembly provided in accordance with the present disclosure is shown including a jaw member generally identified by reference numeral 1120. Jaw member 1120 includes a jaw frame 1122 and a disposable component 1220 releasably engageable thereon, e.g., slidably positionable thereon. A complementary jaw member (not shown) substantially similar to jaw member 1120 and configured to oppose jaw member 1120 is also provided, but will not be described herein to avoid unnecessary repetition. As can be appreciated, the jaw members cooperate to pivot between a spaced-apart position and an approximated position for grasping tissue therebetween.

With continued reference to FIGS. 10 and 11, jaw member 1120 includes a jaw frame 1122 and a disposable component 1220. Jaw frame 1122 is similar to jaw frame 122 of jaw member 120 and is configured to pivotably engage an opposed jaw member (not shown) such that the jaw members may be moved between a spaced-apart position and an approximated position for grasping tissue therebetween. Further, jaw frame 1122 defines an elongated configuration and includes a divot 1123 formed on a bottom surface 1124 thereof toward a distal end 1125 thereof, the importance of which will be described hereinbelow.

Continuing with reference to FIGS. 10 and 11, disposable component 1220 of jaw member 1120 includes a jaw housing 1222, an insulator 1224, a tissue sealing plate 1226 and an O-ring 1228. Similar to disposable component 220 (FIGS. 3A-5), jaw housing 1222 of disposable component 1220 is configured for slidable positioning about insulator 1224, tissue sealing plate 1226 and jaw frame 1122. More specifically, jaw housing 1222 includes an elongated cavity 1223a defined therein for slidable receiving tissue sealing plate 1226, insulator 1224, and jaw frame 1122 therethrough. Jaw housing 1222 further includes an annular slot 1223b defined therein toward a distal end 1223c thereof for positioning of O-ring 1228 thereon. Annular slot 1223b is configured to align with divot 1123 formed with jaw frame 1122 such that O-ring 1228 may be disposed within both annular slot 1223c defined within jaw housing 1222 and divot 1123 defined within jaw frame 1122 to retain jaw housing 1222 and jaw frame 1122 in fixed relation relative to one another.

Insulator 1224 is substantially similar to insulator 224 (FIG. 4) and is configured to electrically isolate tissue sealing plate 1226 from the remaining components of disposable component 1220. Insulator 1224 includes a base (not shown) and a body portion 1225a extending distally therefrom. The base (not shown) is configured similarly to base 225a of insulator 224 of disposable component 220 of jaw member 120 (FIGS. 3A-4). In particular, the base (not shown) is configured to abut a proximal end 1227a of tissue sealing plate 1226 on an upper side thereof and to abut proximal end 1126 of jaw frame 1122 on the lower side thereof. The base (not shown) may also be configured to set a gap distance "g" (FIG. 3B) between the jaw members similarly as described above with respect to end effector assembly 100 (see FIGS. 3A-7).

However, different from insulator 224 (FIG. 4), insulator 1224 further includes an annular slot 1225b defined therein toward a distal end 1225c thereof and configured to align with annular slot 1223b defined within jaw housing 1222 and divot 1123 defined within jaw frame 1122. Annular slot 1225b is configured to receive at least a portion of O-ring 1228 therein such that, as will be described in greater detail below, O-ring 1228 may be used to secure jaw housing 1222, jaw frame 1122, and insulator 1224 in fixed relation relative to one another.

With continued reference to FIGS. 10-11, tissue sealing plate 1226 of disposable component 1220 is configured for positioning about insulator 1224 and for slidable insertion into jaw housing 1222. More specifically, tissue sealing plate 1226 includes a lip 1227b extending from an outer periphery thereof that is configured to engage a track 1225d defined within insulator 1224 to retain tissue sealing plate 1226 and insulator 1224 in fixed position relative to one another. Tissue sealing plate 1226 further includes a post 1227c extending therefrom that is configured to electrically connect tissue sealing plate 1226 to a source of electrosurgical energy (not shown), e.g., via wires 312 (FIG. 1) disposed within electrosurgical cable 310 (FIG. 1).

O-ring 1228, as mentioned above, is configured for positioning within annular slot 1223b of housing 1222, annular slot 1225b formed within insulator 1224, and divot 1123 formed within jaw frame 1122 such that, upon positioning of O-ring 1228 about jaw housing 1222, insulator 1224 and jaw frame 1122, O-ring retains jaw housing 1222, insulator 1224, jaw frame 1122, and tissue sealing plate 1226 (which is retained in fixed position relative to insulator 1224) in substantially fixed relation relative to one another. As can be appreciated, similar to O-ring 228 of jaw member 120 (FIGS. 3A-5), O-ring 1228 defines the gap distance "g" (FIG. 3B) between the jaw members when moved to the approximated position. Thus, in the embodiment of jaw member 1120, O-ring 1228 performs two functions: to secure disposable component 1220 of jaw member 1120 and the sub-components thereof to jaw frame 1122 in fixed relation relative to one another, and to set the gap distance "g" (FIG. 3B) between the jaw members upon movement of the jaw members to an approximated position, as discussed above with regard to O-ring 228 of disposable component 220 of jaw member 120. O-ring 1228 may otherwise be configured similarly to O-ring 228 (see FIGS. 3A-5).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:

an end effector assembly including first and second jaw members defining respective proximal and distal ends, the first and second jaw members coupled to each other at the respective proximal ends thereof such that at least one of the first and second jaw members is movable relative to the other between a spaced-apart position and an approximated position for grasping tissue therebetween, at least one of the jaw members including:

an electrically-conductive plate disposed between the proximal and distal ends of the at least one jaw member and spaced-apart from the distal end thereof;

a jaw housing supporting the plate thereon, the jaw housing including a distal portion disposed between the electrically-conductive plate and the distal end of the at least one jaw member; and a ring member surrounding the distal portion of the jaw housing, the ring member distally-spaced from the plate and extending beyond the plate towards the other jaw member such that, in the approximated position of the first and second jaw members, the ring member contacts a portion of the other jaw member to define a gap distance between the plate and the other jaw member.

2. The forceps according to claim 1, wherein the gap distance is in a range of about 0.001 inches to about 0.006 inches.

3. The forceps according to claim 1, wherein the ring member is elastomeric and is configured to resiliently compress upon contact with the portion of the other jaw member.

4. The forceps according to claim 1, wherein the ring member is releasably positionable about the jaw housing.

5. The forceps according to claim 1, wherein the at least one jaw member further includes an insulating member disposed within the jaw housing, and wherein the ring member is positioned to surround a portion of the insulating member.

6. The forceps according to claim 5, wherein the at least one jaw member further includes a jaw frame disposed within the jaw housing, the jaw frame supporting the insulating member thereon, and wherein the ring member is positioned to surround a portion of the jaw frame.

7. The forceps according to claim 1, wherein the jaw housing defines an annular groove and wherein the ring member is positioned within the annular groove.

8. The forceps according to claim 1, wherein the jaw housing defines a longitudinal axis and wherein the ring member is longitudinally-spaced from the plate.

9. The forceps according to claim 1, wherein at least one of the first and second jaw members is adapted to connect to a source of energy for applying energy to tissue grasped between the first and second jaw members.

10. A forceps, comprising:

an end effector assembly including first and second jaw members defining respective proximal and distal ends, the first and second jaw members coupled to each other at the respective proximal ends thereof such that at least one of the first and second jaw members is movable relative to the other between a spaced-apart position and an approximated position for grasping tissue therebetween, at least one of the jaw members including:

a jaw frame;

an electrically-conductive plate disposed between the proximal and distal ends of the at least one jaw member and spaced-apart from the distal end thereof;

a jaw housing supporting the plate thereon and disposed about the jaw frame, the jaw housing including a distal portion disposed between the electrically-conductive plate and the distal end of the at least one jaw member; and a ring member surrounding the distal portion of the jaw housing and retaining the jaw housing about the jaw frame, the ring member distally-spaced from the plate and extending from the plate towards the other jaw member such that, in the approximated position of the first and second jaw members, the ring member contacts a portion of the other jaw member to define a gap distance between the plate and the other jaw member.

11. The forceps according to claim 10, wherein the gap distance is in a range of about 0.001 inches to about 0.006 inches.

12. The forceps according to claim 10, wherein the ring member is elastomeric, the ring member configured to resiliently retain the jaw housing about the jaw frame and to resiliently compress upon contact with the portion of the other jaw member.

13. The forceps according to claim 10, wherein the ring member is releasably positionable about the jaw housing.

14. The forceps according to claim 10, wherein the at least one jaw member further includes an insulating member disposed within the jaw housing, and wherein the ring member retains the jaw housing about insulating member.

15. The forceps according to claim 14, wherein the ring member is positioned to surround a portion of the insulating member.

16. The forceps according to claim 10, wherein the jaw housing defines an annular groove and wherein the ring member is positioned within the annular groove.

17. The forceps according to claim 10, wherein the jaw housing defines a longitudinal axis and wherein the ring member is longitudinally-spaced from the plate.

18. The forceps according to claim 10, wherein at least one of the first and second jaw members is adapted to connect to a source of energy for applying energy to tissue grasped between the first and second jaw members.

*19. A forceps, comprising:*

*an end effector assembly including first and second jaw members defining respective proximal and distal ends, the first and second jaw members coupled to each other at the respective proximal ends thereof such that at least one of the first or second jaw members is movable relative to the other between a spaced-apart position and an approximated position for grasping tissue therebetween, the first jaw member including:*

*an electrically-conductive plate disposed between the proximal and distal ends of the first jaw member and spaced-apart from the distal end thereof;*

*a jaw housing supporting the electrically-conductive plate thereon, the jaw housing including a distal portion disposed between the electrically-conductive plate and the distal end of the first jaw member; and*

*a gap distance control member disposed at the distal portion of the jaw housing, the gap distance control member distally-spaced from the electrically-conductive plate and extending beyond the electrically-conductive plate towards the second jaw member such that, in the approximated position of the first*

*and second jaw members, the gap distance control member contacts a portion of the second jaw member to define a gap distance between the electrically-conductive plate and the second jaw member.*

*20. The forceps according to claim 19, wherein the gap distance control member is insulative.*

*21. The forceps according to claim 19, wherein the gap distance control member is elastomeric.*

*22. The forceps according to claim 19, wherein the gap distance control member surrounds the distal portion of the jaw housing.*

*23. The forceps according to claim 22, wherein the gap distance control member is configured as a ring surrounding the distal portion of the jaw housing.*

*24. The forceps according to claim 19, wherein the second jaw member includes:*

*an electrically-conductive plate disposed between the proximal and distal ends of the second jaw member and spaced-apart from the distal end of the second jaw member;*

*a jaw housing supporting the electrically-conductive plate thereon, the jaw housing including a distal portion disposed between the electrically-conductive plate and the distal end of the second jaw member; and*

*a gap distance control member disposed at the distal portion of the jaw housing, the gap distance control member distally-spaced from the electrically-conductive plate and extending beyond the electrically-conductive plate towards the first jaw member such that, in the approximated position of the first and second jaw members, the gap distance control members of the first and second jaw members contact one another to define a gap distance between the electrically-conductive plates thereof.*

* * * * *